(12) United States Patent
Yamamoto et al.

(10) Patent No.: US 6,947,779 B2
(45) Date of Patent: Sep. 20, 2005

(54) OPTICAL MEASUREMENT DEVICE

(75) Inventors: Tsuyoshi Yamamoto, Hatoyama (JP); Atsushi Maki, Hachioji (JP); Hideaki Koizumi, Tokyo (JP)

(73) Assignees: Hitachi, Ltd., Tokyo (JP); Hitachi Medical Corporation, Tokyo (JP)

( * ) Notice: Subject to any disclaimer, the term of this patent is extended or adjusted under 35 U.S.C. 154(b) by 155 days.

(21) Appl. No.: 09/873,206

(22) Filed: Jun. 5, 2001

(65) Prior Publication Data

US 2002/0183603 A1 Dec. 5, 2002

Related U.S. Application Data (63) Continuation of application No. PCT/JP99/06749, filed on Dec. 1, 1999.

(30) Foreign Application Priority Data

Dec. 7, 1998 (JP) .......................................... 10-347299

(51) Int. Cl.[7] .............................................. A61B 5/00
(52) U.S. Cl. ........................ 600/323; 600/407; 600/473
(58) Field of Search ................................ 600/323, 425, 600/427, 316, 347, 407, 473, 476, 328, 431; 250/227.2, 341.1; 378/4, 63; 356/39, 320, 364, 368, 435, 447

(56) References Cited

U.S. PATENT DOCUMENTS

| 5,419,320 | A | * | 5/1995 | Kawaguchi et al. ...... 250/341.1 |
| 5,448,992 | A | * | 9/1995 | Kupershmidt ................ 356/364 |
| 5,803,909 | A | * | 9/1998 | Maki et al. .................. 600/310 |
| 6,240,309 | B1 | * | 5/2001 | Yamashita et al. ........ 250/227.2 |
| 6,397,099 | B1 | * | 5/2002 | Chance ........................ 600/323 |

FOREIGN PATENT DOCUMENTS

| JP | A-59-75785 | 10/1982 |
| JP | A-4-307605 | 4/1991 |
| JP | A-5-115485 | 10/1991 |
| JP | A-8-154924 | 12/1994 |
| JP | A-8-215179 | 2/1995 |
| JP | A-9-19408 | 7/1995 |
| JP | 9-98972 | 10/1995 |
| JP | A-9-149903 | 11/1995 |

OTHER PUBLICATIONS

Yuichi Yamashita, Atsushi Maki and Hideaki Koizumi, *Near-infrared topographic measurement system: Imaging of absorbers localized in a scattering medium*; 1996 American Institute of Physics, Rev. Sci, Instrum. 67 (3), Mar. 1996, pp. 730–732.

Patrick W. McCormick, M.D., Melville Stewart, M.S., Gary Lewis, E.E., Manuel Dujovny, M.D., and James I. Ausman, M.D., Ph.D., *Intracerebral penetration of infrared light*; J. Neurosurg/vol. 76/Feb. 1992; pp. 315–318.

Atushi Maki, Yuichi Yamashita and Yoshitoshi Ito, *Spatial and temporal analysis of human motor activity using non-invasive NIR topography*; Medical Physics, Dec. 1995, vol. 22, No. 12; pp. 1997–2005.

* cited by examiner

*Primary Examiner*—Tu Hoang
(74) *Attorney, Agent, or Firm*—Reed Smith LLP; Stanley P. Fisher, Esq.; Juan Carlos A. Marquez, Esq.

(57) ABSTRACT

Optical measurement that is optimum for improving spatial resolution is accomplished by making it possible to estimate a physical quantity of an object substance to be measured at any point on a subject. When any position to be evaluated, in an image shown in a window 1-1, is pointed and selected a mouse pointer 1-4, the value of the concentration or its change of the object substance at the point is displayed in the display area 1-7 of a window 1-3. The drawings represents an example in which one position is specified and there are two object substances to be measured. The value of the concentration or its change of each object substance to be measured is separately displayed.

17 Claims, 10 Drawing Sheets

Prior Art

FIG. 13

OPTICAL MEASUREMENT DEVICE

This application is a continuation application of and claims the priority date of the PCT application number PCT/JP99/06749 filed on Dec. 1, 1999, which designates the United States of America, under 35 U.S.C.§120.

FIELD OF THE INVENTION

The present invention relates to an optical measurement device and, more specifically, relates to an optical measurement device which is suitable for obtaining metabolic information in vivo.

BACKGROUND ART

As a somatometry using light, an optical topography which is used for measuring brain function has been known as disclosed, for example, in Japanese Patent Publication Nos. JP-A-9-98972 and JP-A-5-115485. In such optical topography, light is illuminated on a living body representing a measurement object (a subject), and transmitted and scattered light from the tissue in vivo is collected and detected at a point remote from the illumination point by a few mm to a few cm. An optical fiber is generally used as a light guiding means when illuminating light onto a living body and detecting light from the living body. From the measured intensity of the transmitted and scattered light from the tissue in vivo a density of light absorption substance in vivo can be determined. As examples of such light absorption substances oxyhemoglobin and deoxyhemoglobin representing metabolic substances in vivo are enumerated. When determining the density of a light absorption substances, the light absorption characteristics of the light absorption substance corresponding to the wavelength of the illuminate light are used. In general, when measuring a deep portion in a living body, a light having a wavelength in a range from 650 mm to 1300 mm is used which shows a high in vivo transmissivity.

Figure 13:
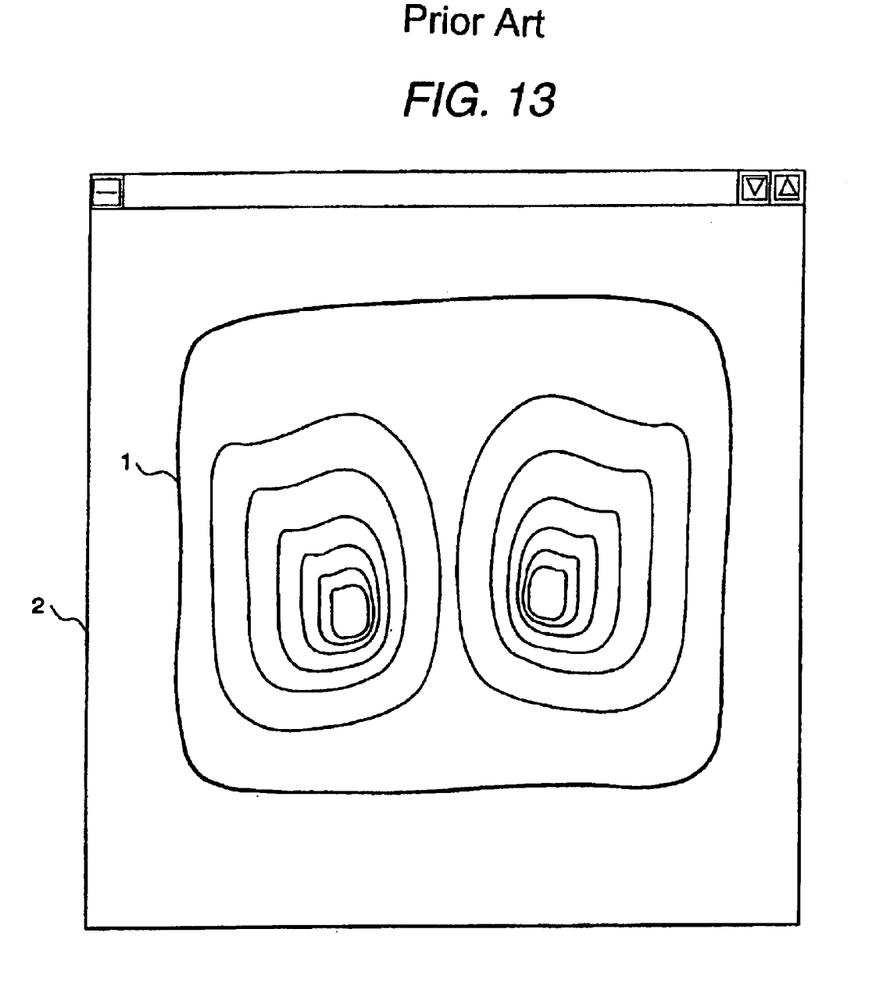
FIG. 13 is a diagram showing a conventional topographic image displayed on a display unit in an optical measurement device.

FIG. 13 shows a conventional topographic image displayed on a display unit in an in vivo optical measurement device. A topographic image 1 representing a physical quantity of in vivo metabolic substance within a measurement region is shown in a window 2. The present image displays a distribution of measured amount or its variation of the in vivo metabolic substance which was obtained by illuminating a laser beam having a certain wavelength onto a tissue in vivo and by making use of the intensity of the transmitted and scattered light from the tissue in vivo and of the absorbance of the metabolic substance at the wavelength of the laser beam used. The interval between the laser beam illumination point and the detection point of the in vivo tissue transmitting light intensity, namely the interval between the measurement points is about a few cm which varies depending on the scattering characteristic of the tissue in vivo. Therefore, a measured amount or its variation of an in vivo metabolic substance at between measurement points is estimated by a statistical processing, for example, by interpolation.

In order to obtain detailed information on tissue in vivo a high spatial resolution is necessitated. However, a resolution of a present day in vivo optical measurement device is low and is about a few cm. Namely, when imaging a physical quantity of an in vivo metabolic substance, an imaging processing is performed through a statistical processing like a linear interpolation, however, a data at a point between measurement points can not be displayed and it was impossible to obtain a numerical information (a quantitative information) at the intermediate point. For this reason, it was difficult to obtain a detailed information of the in vivo tissue.

DISCLOSURE OF THE INVENTION

An object of the present invention is to provide an optical measurement device which permits an evaluation of a measured quantity or its variation of a measurement object substance at any point including a measurement point and points other than the measurement point within a measurement region of a subject and is, thereby, suitable for enhancing a spatial resolution thereof.

According to the present invention, the measurement object substance within the measurement region of the subject is measured optically.

Further, when one of any points within the measurement region is designated, a measured quantity of the measurement object substance at the designated point, the variation of the measured quantity or time dependency information of either one or information about the designated point is presented.

PREFERRED EMBODIMENT FOR REDUCING THE INVENTION INTO PRACTICE

Figure 9:
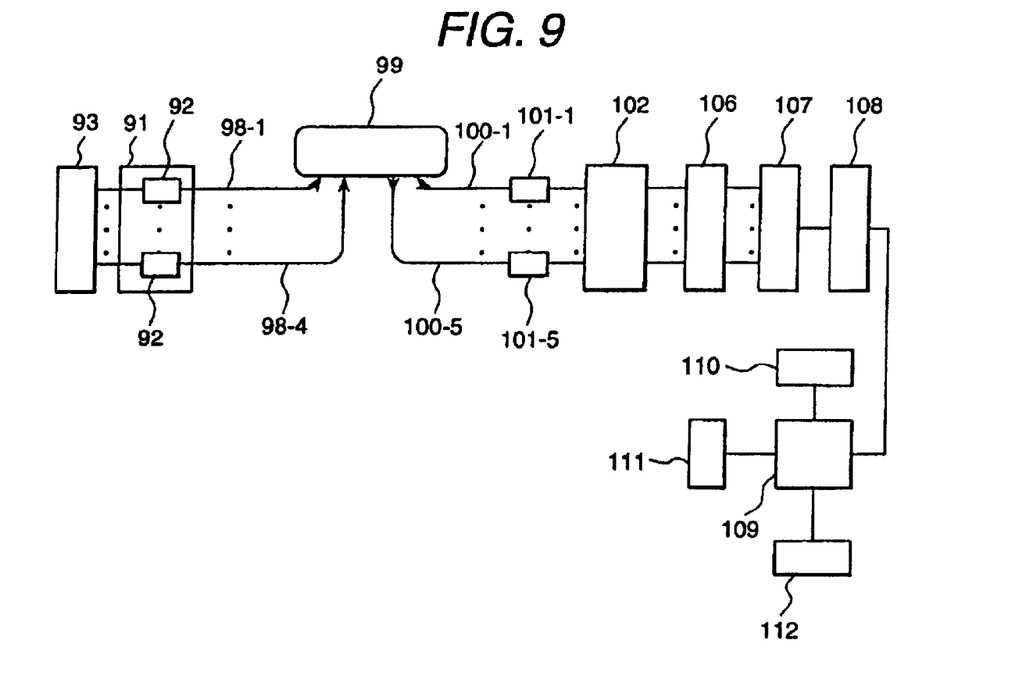
FIG. 9 is a block diagram showing a structure of a major portion of one embodiment of an optical measurement device to which the present invention is applied.

FIG. 9 is a block diagram showing a structure of a major portion of one embodiment of an optical measurement device to which the present invention is applied. In the present embodiment, an example, in which a light is illuminated onto a skin of, for example, a head of a subject representing a measurement object and through detection of light scattered in the subject in response to the illumination and transmitted through the subject an intracerebrum or a cortex cerebri is imaged, is shown by making use of an instance wherein number of measurement channels, namely number of measurement points is 12 and number of signals to be measured (a number of analogue/digital conversion channels) is 24. Of course, the present invention is not limited as its measurement object to the head, but is applicable to other portions, and further can be applied to other than a living body.

A light source 91 is constituted by four pieces of optical modules 92. Each of the optical modules 92 is constituted by two pieces of semiconductor lasers each of which radiates light having a plurality of wavelengths within a wavelength range from visible light to infrared light, for example, light of two wavelengths of 780 nm and 830 nm. The values of two wavelengths are not limited to 780 nm and 830 nm, further, number of wavelengths included is not limited to two. For the optical source 91 photo emitting diodes can be used instead of the semiconductor lasers. Lights from all of the eight semiconductor lasers included in the optical source 91 are respectively modulated by an oscillator unit 93 constituted by eight oscillators each having a different oscillation frequency.

Figure 10:
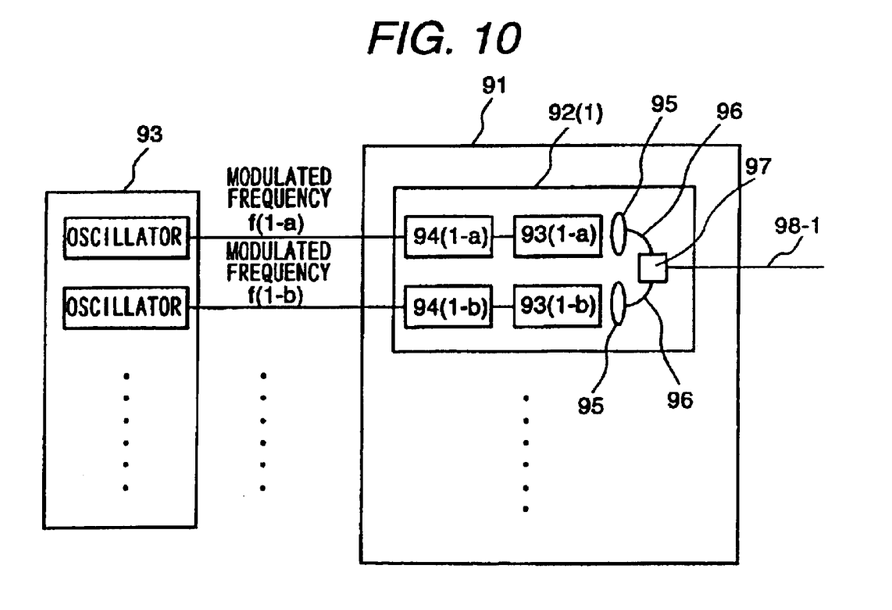
FIG. 10 is a block diagram showing a structure within an optical module in FIG. 9 device.

FIG. 10 shows a structure within the optical module 92 while referring to an optical module 92(1) as an example. In the optical module 92(1), a semiconductor laser 93(1-a) and 93(1-b) and driver circuits 94(1-a) and 94(1-b) for the respective semiconductor lasers are included. Herein, with regard to letters in the above brackets, the numerals represent a serial number of the optical modules included, and a and b represent respectively wavelength of 780 nm and wavelength of 830 nm. These semiconductor laser driver circuits 94(1-a) and 94(1-b) supply a DC bias current for the semiconductor laser 93(1-a) and 93(1-b) as well as application of signals having respectively different frequencies f(1-a) and f(1-b) from the oscillator 93 provides modulation to the lights radiated from the semiconductor lasers 93(1-a) and 93(1-b). As such modulation, an instance of an analogue modulation with a sinusoidal waves is shown in the present embodiment, however, a digital modulation with rectangular waves having respectively different time intervals, namely a digital modulation in which light is flashed in different time intervals can, of course, be used. Thus modulated light beams are individually introduced for every semiconductor laser via condenser lenses 95 to respective optical fibers 96. The lights having the two wavelengths introduced into the individual optical fibers are introduced for every optical module 92 via an optical fiber coupler 97 into a single optical fiber, for example, into an illumination use optical fiber 98-1. Light beams with two wavelengths for every optical module are introduced into illumination use optical fibers 98-1 through 98-4, and from the other terminals of these illumination use optical fibers the lights are illuminated at four different illumination points on the surface of subject 99. The light scattered in the subject and passed through the subject is detected by photo diodes 101-1 through 101-5 through detection use optical fibers 100-1 through 100-5 which are arranged at five detection points on the surface of the subject 99. The end faces of these optical fibers touch softy onto the surface of the subject 99, and, for example, the optical fibers are attached to the subject 99 by means of probes as disclosed in JP-A-9-149903.

Figure 11:
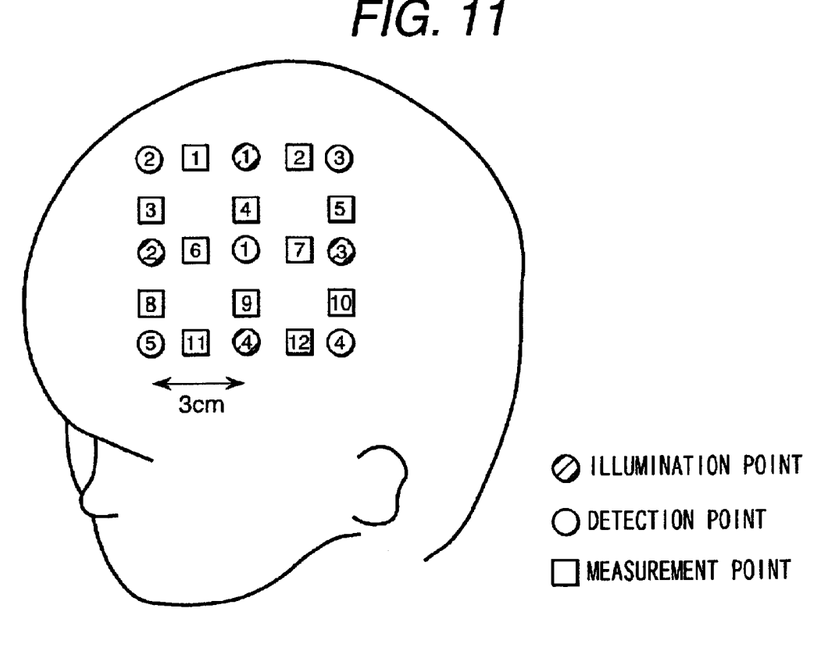
FIG. 11 is a diagram showing an example of a geometric arrangement of illumination points and detection points on the surface of a subject.

FIG. 11 shows an example of geometric arrangement of the illumination points 1 through 4 and the detection points 1 through 5 on the surface of the subject 99. In the present embodiment, the illumination and detection position are alternatively arranged on square shaped grids. If intermediate points between adjacent illumination and detection points are determined as measurement points, there are 12 combinations of the adjacent illumination and detection points, therefore, the number of measurement points, namely the number of measurement channels is determined as 12. Such arrangement of the illumination and detection points are disclosed, for example, in JP-A-9-149903 and Yuichi Yamashita et al. "Near-infrared topographic measurement system: Imaging of absorbers localized in a scattering medium" (Rev. Sci. Instrum. 67(3), March 1996, pp730–732). When setting the interval between the adjacent illumination and detection points as 3 cm, the lights detected from the respective detection points contains information on a brain collected by the lights passing through the skin and skull as, for example, reported by Patric W. McCormic et al. "Intracerebral penetration of infrared light" (J. Neurosurg./ Volume 76/February 1992. pp315–318).

Based on the hitherto description, when 12 measurement channels are set through the arrangement of the illumination and detection points as shown in FIG. 11, measurement of a brain in a total region of 6 cm×6 cm can be performed.

In the present embodiment, for the sake of simplicity a case in which the number of measurement channels is 12 is exemplified, however, when the number of illumination points and detection points arranged in a grid shape is further increased to increase the number of measurement channels, the measurement region can be enlarged.

In FIG. 9, the lights detected by the respective detection use optical fibers 100-1 through 100-5 are detected by independent five photo detectors, for example, by photo diodes 101-1 through 101-5 for every detection point, namely for every detection use optical fiber corresponding to each of the detection points. As the photo diodes avalanche type photo diodes are preferable which can realize an optical measurement with a high sensitivity. Further, as the photo detector a photo multiplier tube can be used. After converting the optical signals into electrical signals with these photo diodes, with a detection circuit which performs selective detection of the modulated signals, for example, with a lock-in amplifier module 102 constituted by a plurality of lock-in amplifiers, modulation signals corresponding to the illumination positions and the wavelengths are selectively detected.

In the present embodiment, a lock-in amplifier is shown as the modulation signal detection circuit meeting the instance of analogue modulation, however, when a digital modulation is used, a digital filter or a digital signal processor is to be used for the modulation signal detection.

Figure 12:
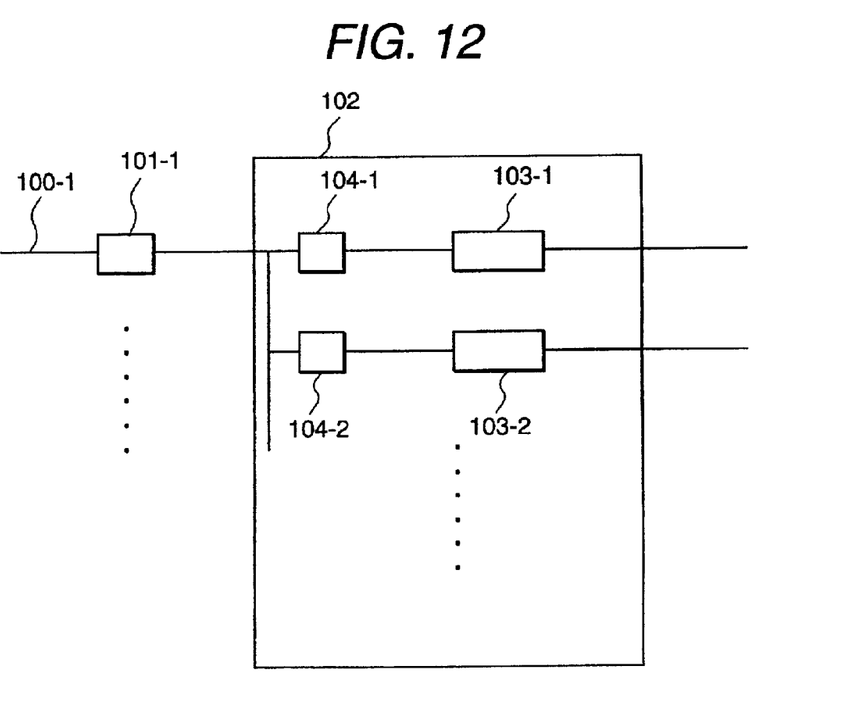
FIG. 12 is a block diagram showing a structure of a lock-in amplifier module in FIG. 9 device.

FIG. 12 shows a structure of the lock-in amplifier module 102 as shown in FIG. 9. At first, modulation signal separation of detection signals detected by the photo diode 101-1 in FIG. 11 will be explained. From "detection point 1" lights illuminated onto the adjacent "illumination point 1", "illumination point 2", "illumination point 3" and "illumination point 4" can be detected, therefore, "measurement point 4", "measurement point 6", "measurement point 7" and "measurement point 9" in FIG. 11 assume the measurement object points. Herein, the light from "detection point 1" detected by the photo diode 101-1 contains eight signal components having modulation frequencies f(1-a), f(1-b), f(2-a), f(2-b), f(3-a), f(3-b), f(4-a) and f(4-b) corresponding to respective lights each having two wavelengths illuminated at "illumination point 1", "illumination point 2", "illumination point 3" and "illumination point 4". The optical signal containing these eight signal components is introduced via eight amplifiers 104-1 through 104-8 to eight lock-in amplifiers 103-1 through 103-8. The eight lock-in amplifiers 103-1 through 103-8 are respectively provided with the signals having modulation frequencies f(1-a), f(1-b), f(2-a), f(2-b), f(3-a), f(3-b), f(4-a) and f(4-b) as reference signals. Accordingly, the optical signal component of 780 nm and 830 nm illuminated onto "illumination point 1" is selectively separated by the lock-in amplifiers 103-1 and 103-2 and lock-in detected, the optical signal component of 780 nm and 830 nm illuminated onto "illumination point 2" is selectively separated by the lock-in amplifiers 103-3 and 103-4 and lock-in detected, the optical signal component of 780 nm and 830 nm illuminated onto "illumination point 3" is selectively separated by the lock-in amplifiers 103-5 and 103-6 and lock-in detected, and the optical signal component of 780 nm and 830 nm illuminated onto "illumination point 4" is selectively separated by the lock-in amplifiers 103-7 and 103-8 and lock-in detected.

With regard to detection signals from "detection point 2", "detection point 3", "detection point 4" and "detection point 5" detected respectively by the photo diodes 101-2 through 101-5, desired optical signal components are selectively separated and lock-in detected in the like manner as above. Namely, the optical signal from "detection point 2" detected by the photo diode 101-2 is introduced via the four amplifiers 104-9 through 104-12 into the four lock-in amplifiers 103-9 through 103-12, and is selectively separated therein into the optical signal component of 780 nm and 830 nm illuminated onto "illumination point 1" and the optical signal component of 780 nm and 830 nm illuminated onto "illumination point 2" and is lock-in detected, the optical signal from "detection point 3" detected by the photo diode 101-3 is introduced via the four amplifiers 104-13 through 104-16 into the four lock-in amplifiers 103-13 through 103-16, and is selectively separated therein into the optical signal component of 780 nm and 830 nm illuminated onto "illumination point 1" and the optical signal component of 780 nm and 830 nm illuminated onto "illumination point 3" and is lock-in detected, the optical signal from "detection point 4" detected by the photo diode 101-4 is introduced via the four amplifiers 104-17 through 104-20 into the four lock-in amplifiers 103-17 through 103-20, and is selectively separated therein into the optical signal component of 780 nm and 830 nm illuminated onto "illumination point 3" and the optical signal component of 780 nm and 830 nm illuminated onto "illumination point 4" and is lock-in detected, and the optical signal from "detection point 5" detected by the photo diode 101-5 is introduced via the four amplifiers 104-21 through 104-24 into the four lock-in amplifiers 103-21 through 103-24, and is selectively separated therein into the optical signal component of 780 nm and 830 nm illuminated onto "illumination point 2" and the optical signal component of 780 nm and 830 nm illuminated onto "illumination point 4" and is lock-in detected.

Further, as will be apparent from FIG. 11, when the detection points are respectively at "detection point 2", "detection point 3", "detection point 4" and "detection point 5", their corresponding measurement object points are respectively "measurement point 1" and "measurement point 3", "measurement point 2" and "measurement point 5", "measurement point 10" and "measurement point 12" and "measurement point 8" and "measurement point 11".

As has been explained above, when number of wavelengths contained is two and the number of measurement points is 12, the number of measurement signals assumes 24, 24 pieces of lock-in amplifiers 103-1 through 103-24 in total are used in the lock-in amplifier module 102. Analogue output signals outputted from these lock-in amplifiers 103-1 through 103-24 (channels 1 through 24) are respectively accumulated for a predetermined time by each of sample hold circuits of corresponding channels in a sample hold circuit module 106. After ending the accumulation, a switch (multiplexer) 107 is successively changed over and the signals stored in the respective sample hold circuits are converted into digital signals, for example, by an 12 bit analogue/digital converter (A/D converter) 108, then the converted signals for all of the channels are stored in a memory unit 110 disposed outside a computer 109. Of course, the storage can be effected in a memory unit inside the computer 109.

When the sample hold circuit module 106 is not employed, the switch 107 is repeatedly changed over at a high speed. In such instance, the analogue signals of respective channels are converted for every change-over into digital signals by the analogue/digital converter 108 to store the same in the memory unit 110, and the digital signals obtained for a predetermined times are averaged for every channel by the computer 109 to store the same in the memory unit 110. With this measure too, noises in high frequency components can be reduced.

Based on the data stored, the computer 109 computes concentrations of oxyhemoglobin and deoxyhemoglobin representing in vivo metabolic substances (measurement object substances) and further concentration of entire hemoglobin representing the total concentration of these hemoglobins according to the methods disclosed in JP-A-9-19408 and Atsushi Maki et al. "Spatial and temporal analysis of human motor activity using noninvasive NIR topograph" (Med. Phys. 22(12), December 1995, pp 1997–2005), and can display an information presenting portion 111 a topographic image of the measured amount and its variation as well as a graph representing time dependent variation thereof. In this instance, measurement amount and its variation of the measurement object substance at any point between the measurement points are estimated by the computer 109 through a statistic processing, more specifically a linear interpolation processing called as a spline processing, based on the signals obtained at the detection points. The information presenting portion 111 includes a display unit which displays such as a topographic image of a measurement region of the subject, measurement amount or its variation of the measurement object substance at any point within the measurement region and positional information thereof. The information presenting portion 111 can further includes other than the display unit means for presenting the measurement amount or its variation of the measurement object substance at any point within the measurement region and the positional information thereof to a data analyzing personal serving as an operator, specifically, for example, audio output unit.

In FIG. 9, an operation unit 112 is connected to the computer 109 and includes an input means which permits data input outside from the optical measurement device and includes a key board which permits to input letter information such as symbols and numerals through key pressing and a pointing device. The pointing device causes to display a pointer such as an arrow which designates any point on a screen image of the display unit in the information presenting portion 111 and includes a mouse which permits selection of the designated point through operation called as click. Instead of the mouse, the pointing device can be a touch panel (touch screen) which permits selection of the portion touched.

Figure 1:
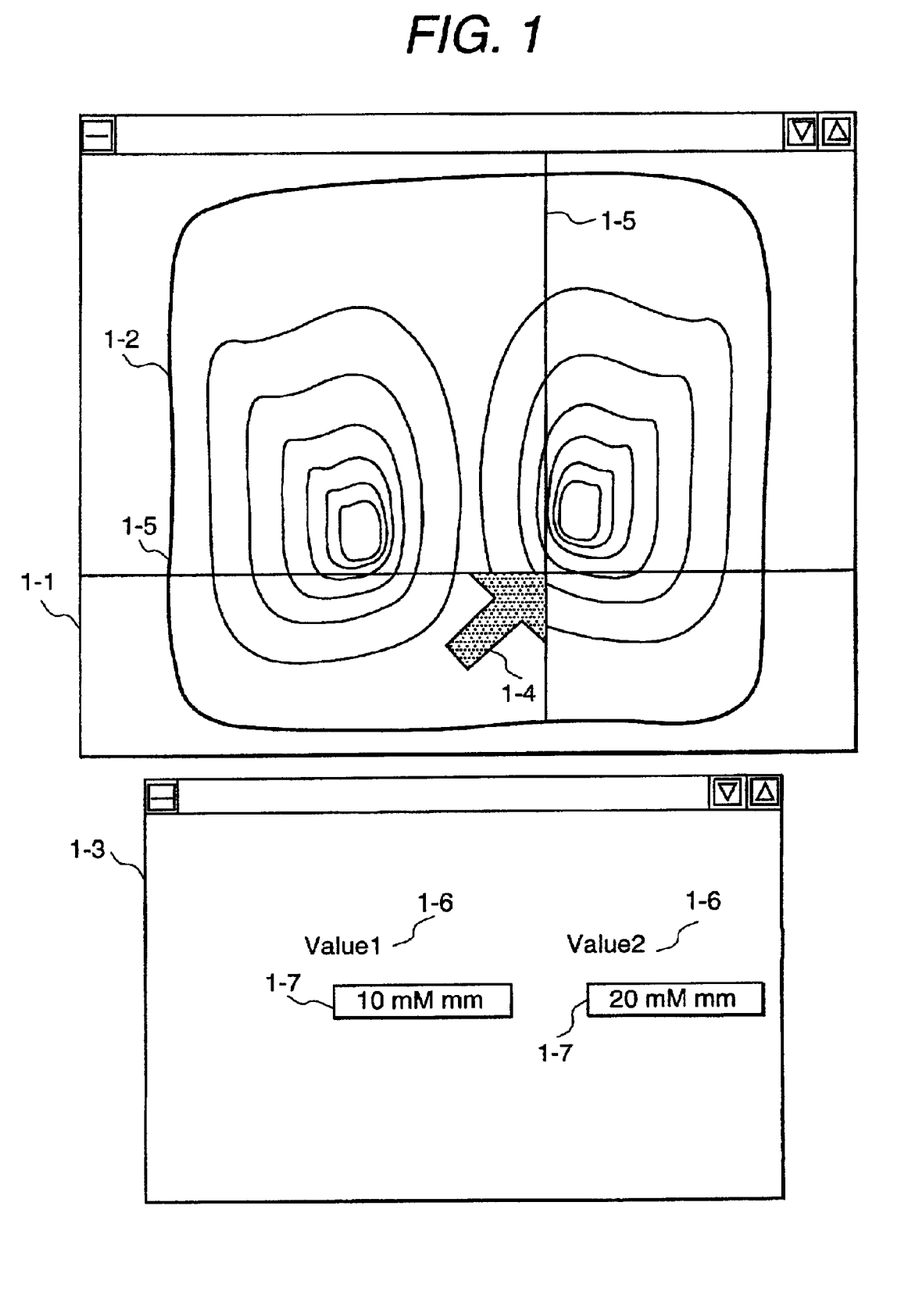
FIG. 1 is a diagram showing an example of a screen image displayed on a display unit in an information presentation portion in FIG. 9.

FIG. 1 shows an example of a screen image displayed on the display unit in the information presenting portion 111 as shown in FIG. 9. 1-1 in the drawing shows a window which includes a topographic image 1-2 illustrating measurement amount or its variation of the measurement object substance in the subject, and 1-3 shows another window displaying the measurement amount and its variation.

The topographic image 1-2 displayed in the window 1-1 is a map shaped figure generated by connecting points (positions) having equal measurement amount or its variation of measurement object substance within the measurement region, and measurement amount and its variation of the measurement object substance at any point between the measurement points are estimated by the computer 109 through a statistic processing, more specifically a linear interpolation processing called as a spline processing, based on the signals obtained at the detection points. 1-4 is an arrow shaped mouse pointer and when the mouse is clicked, the position indicated by the mouse pointer is selected. Such selected position is not limited to the measurement position and can be any position within the measurement region. 1-5 are lines showing supplementarily and visibly the coordinate information in horizontal direction and vertical direction of the position designated by the mouse pointer and these lines move while interlocking with the pointer 1-4. These lines can be any kinds such as solid line, dotted line and broken line. The window 1-3 may displayed always in which the measurement amount, its variation, and time and positional information thereof are displayed, otherwise, may be displayed only when the mouse pointer has been clicked. Further, the mouse pointer 1-4 can be another pointing element having a pen shaped configuration.

In the window 1-3 in which the measurement amount, its variation or the time and positional information thereof is displayed a letter series 1-6 indicating kind of data desired to be displayed and numerical values 1-7 indicating the respective measurement amount and its variation. In FIG. 1, it is possible to display two kinds of measurement amount such as oxyhemoglobin and deoxyhemoglobin, and specifically, FIG. 1 shows an instance when the values thereof are respectively 10 and 20. mM·mm represents a unit with regard to blood quantity.

In the example as shown in FIG. 1, the measurement amount or its variation of the measurement object substances of two kinds is represented by oxyhemoglobin and deoxyhemoglobin at a position desired to be evaluated, however, instead of such example, the measurement amount or its variation of measurement object substance of one kind or three kinds can be displayed.

When the two pieces of windows 1-1 and 1-3 as has been shown in FIG. 1 are displayed in up and down or in light and left relationship so as not to overlap each other, a data processing personnel can easily obtain information visually. Further, these two pieces of windows can be gathered into one. Namely, one of the two windows can be designed to serve other window.

Still further, in case when it is unavoidable to use large windows in FIG. 1 such as when displaying a broad measurement region with a high resolution, the display can be performed by switching the windows 1-1 and 1-3 through command of the data processing personnel. Still further, the window 1-3 can be displayed at the designation position of the pointer 1-4 or adjacent thereof.

The optical measurement device which optically measures the measurement object substance within the measurement region of the subject is constituted so as to operate in such a manner that measurement amount of the measurement object substance at a measurement point is determined based on a detection value of a light illuminated from an illumination point within the measurement region detected at a detection point, a map shaped image formed by connecting points positions) having equal measurement amounts or its variations by making use of the determined measurement amount is displayed on a first image screen, any point on the displayed image is designated and the measurement amount or its variation of the measurement object substance at the designated point is displayed on a second image screen.

The illumination position includes a plurality of points, a light having a plurality of wavelengths is illuminated at respective illumination points, the light components containing signal components of the corresponding number of wavelengths at the illumination points are detected at one detection point and a reference signal is provided for each of light components, thereby, the light components of the respective wavelengths are separated to determine the measurement amount.

The first image screen and the second image screen can be constituted as a single image screen.

Further, the first image screen and the second image screen can be constituted as separate image screens.

Figure 2:
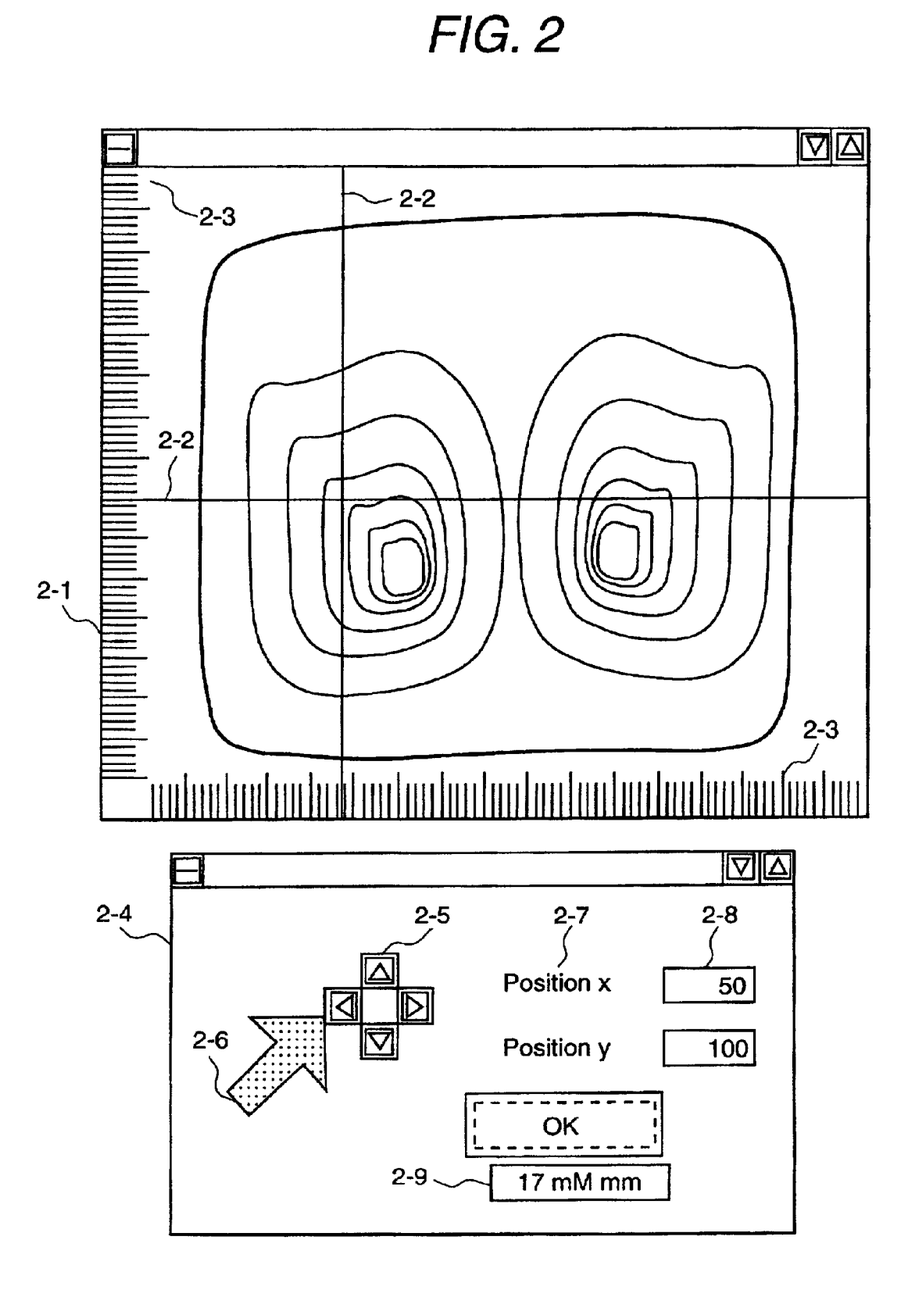
FIG. 2 is a diagram showing another example of a screen image displayed on a display unit in an information presentation portion in FIG. 9.

FIG. 2 shows another example of a screen image displayed on the display unit in the information presenting portion 111 as shown in FIG. 9. On the screen image in a window 2-1, scales 2-3 are provided which permits reading of the positions in horizontal and vertical directions of a crossing point (a crossing position: pointer) of the lines 2-2 in horizontal and vertical directions. The displacement control of the two lines (displacement control of the crossing point of the two lines) can be performed with reference to coordinate values on the screen image displayed in the window 2-4 which displays the measurement amount, its variation or the positional information thereof while confirming the same in the window 2-1. 2-5 represents four buttons which are used to perform the displacement control of the lines 2-2 in horizontal and vertical directions and when a pointer 2-6 designates any of the four buttons 2-5 so as to press the same and the mouse is clicked, the two lines 2-2 namely the crossing point thereof is controlled as desired. 2-7 represents a display region of coordinate information message in horizontal direction (X) and in vertical direction (Y) of the crossing point of the two lines 2-2 which is determined by pressing the buttons 2-5. The coordinate information of the crossing point of the two lines 2-2 is displayed at a coordinate information display region 2-8.

When pressing one of the buttons 2-5, in response thereto the two lines 2-2 displace to a new position and in synchronism therewith the coordinate position values of the crossing point of the two lines 2-2 displayed at the display region 2-8 also change. When the crossing point of the two lines 2-2 reaches the coordinate position which the data analyzing personnel desires, the data analyzing personnel presses an intention confirmation button for processing start by means of an inputting means (for example, a pointing device, key board). Thereby, the processing is started and a measurement amount or its variation of the measurement object substance desired to be displayed is displayed at a measurement amount or its variation display region 2-9.

Instead of pressing the buttons 2-5 for displacing the two lines, the displacement control of the two lines can be performed by pressing keys bearing a similar indication as the buttons 2-5 on the key board. Further, in FIG. 2, the two windows 2-1 and 2-4 are separated each other, however, these windows can be arranged to overlap each other.

Figure 3:
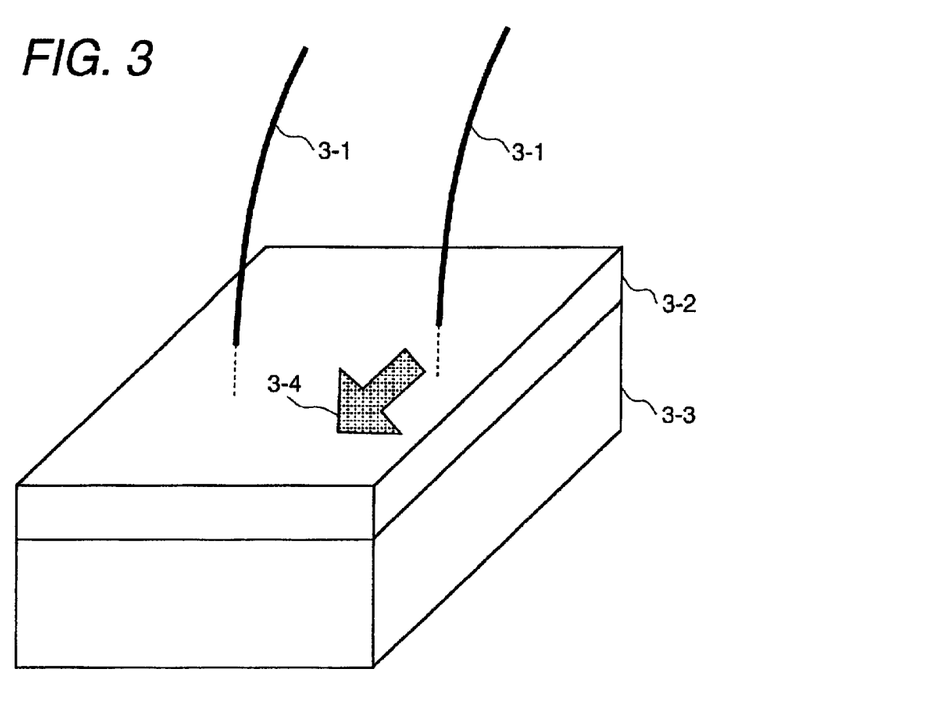
FIG. 3 is a diagram showing another embodiment for designating a point in a measurement region.

FIG. 3 shows another embodiment relating to a method of position designation in a measurement region. The present embodiment is used for designating a position in the measurement region on the subject and for selecting the same. The embodiment in FIG. 3 is shown in a simplified model. Optical fibers 3-1 serving as a light guiding means pass through a sensor made from a piezoelectric element and touch to a subject 3-3. Although two pieces of optical fibers are shown in FIG. 3, one of the two optical fibers corresponds to any one of the illumination use optical fibers 98-1 through 98-4 as shown in FIG. 9, and the remaining one corresponds to any one of the detection use optical fibers 100-1 through 100-5 as shown in FIG. 9. Further, the subject 3-3 corresponds to the subject 99 as shown in FIG. 9. The sensor 3-2 is placed over the subject 3-3 under contact or non-contact condition and is connected to the computer 109 in FIG. 9. When designating any position within the measurement region of the subject 3-3 by means of a designation means 34, the positional signal is received by the sensor 3-2 and is transferred to the computer 109. The designation means 3-4 can be either a pen or a finger.

The optical measurement device which optically measures a measurement object substance within a measurement region of a subject is constituted and operated in such a manner that optical fibers are passed through a sensor made from a piezoelectric element which is placed under contact or non-contact condition on a subject, a measurement position is set on the sensor, a light is illuminated from the optical fiber onto an illumination position within the measurement region, a detection value detected at a detection position is outputted via the optical fiber, thereby, a measurement amount or its variation of the measurement object substance at a measurement position is determined.

The measurement amount and its variation of the measurement object substance at a designated position is displayed in a form of screen image.

Figure 4:
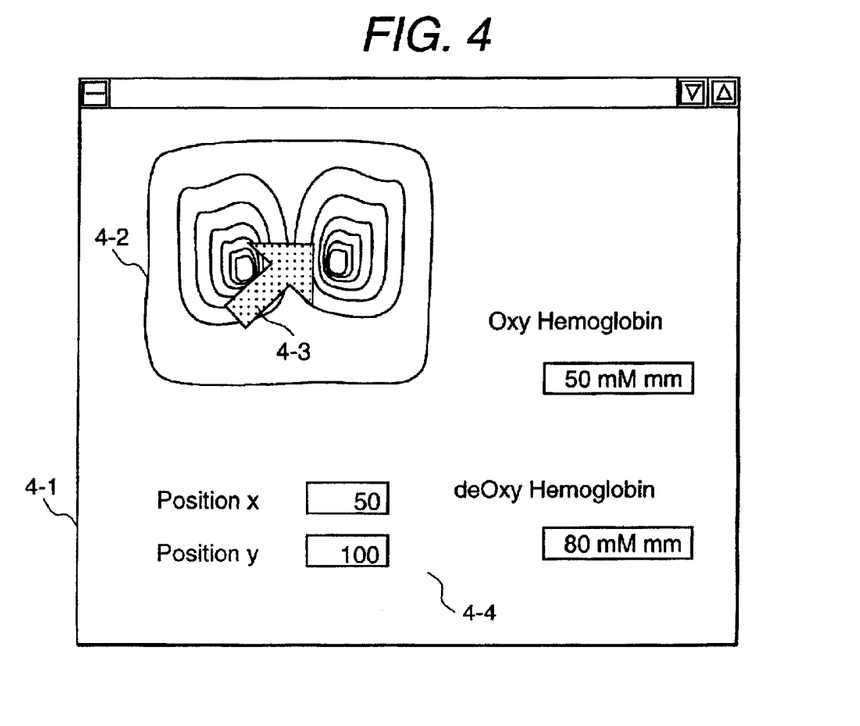
FIG. 4 is a diagram showing still another example of a screen image displayed on a display unit in an information presentation portion in FIG. 9.

FIG. 4 shows still another example of a screen image displayed on a display unit in the information presenting portion 111 in FIG. 9. In a window 4-2 which displays desired data and can freely vary the size thereof, a topographic image 4-2 relating to the measurement region of the subject is displayed. 4-3 represents a pointing means. The pointing means 4-3 can interlock with the pointing device as shown FIG. 3 embodiment. Coordinate values in horizontal and vertical directions of the position designated by the pointer 4-3 are displayed at a display region 4-4, and a measurement amount or its variation of the measurement object substances (specifically, oxyhemoglobin, deoxyhemoglobin and all hemoglobins) at the designated position are displayed at a display region 4-4.

Figure 5:
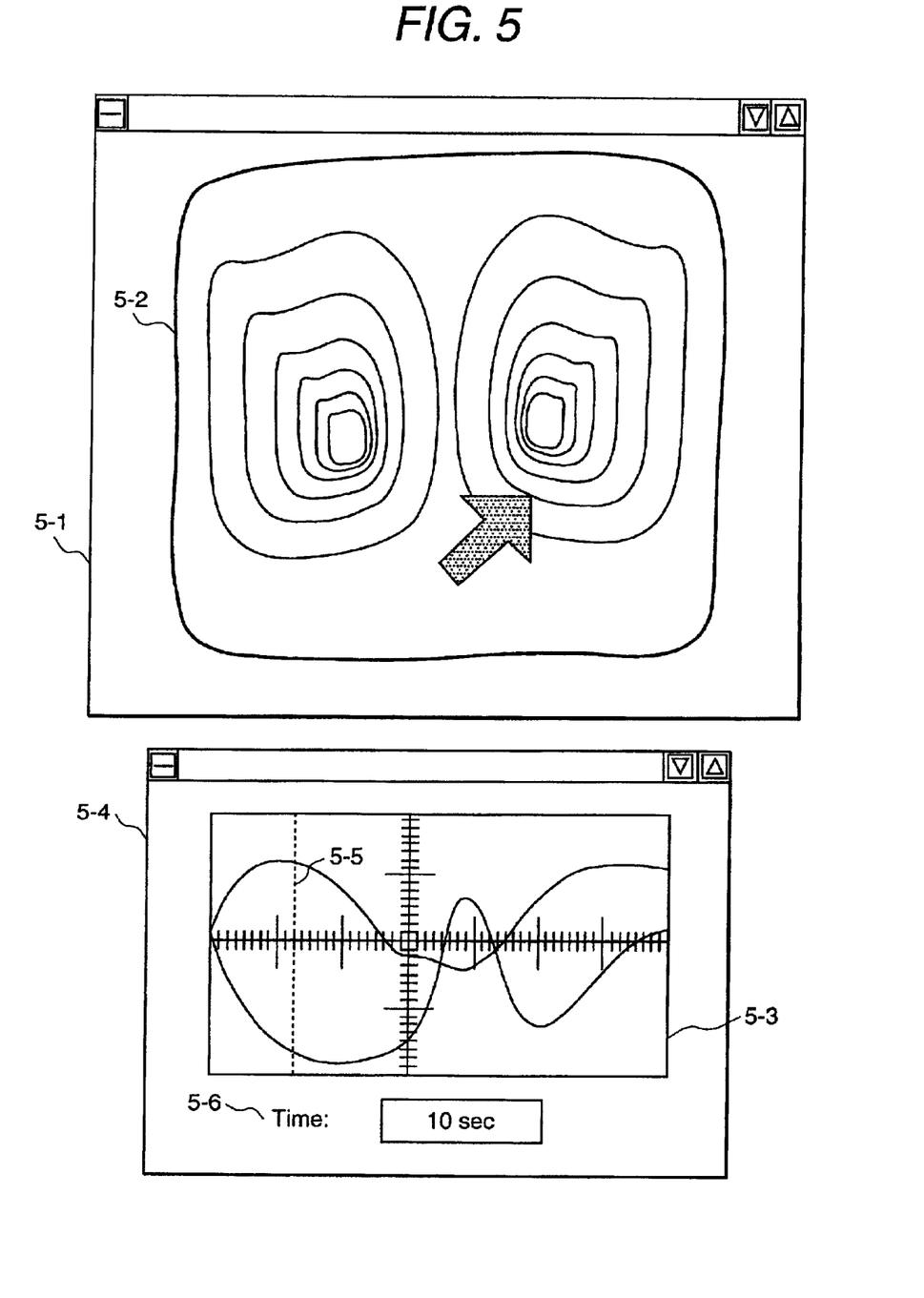
FIG. 5 is a diagram showing a further example of a screen image displayed on a display unit in an information presentation portion in FIG. 9.

FIG. 5 shows a further example of screen images displayed on a display unit in the information presenting portion 111 in FIG. 9. In a window 5-1 a topographic image 5-2 is played, which can be a static topographic image representing an average value of the measurement amounts in a certain measurement time or can be a moving picture representing time dependency of the measurement amount or its variation of the measurement object substance. When any position of the topographic image 5-2 is designated by means of a mouse pointer, a graph representing time dependency of the measurement amount or its variation of the measurement object substance at the designated position, more specifically, a graph 5-3 representing time dependency of oxyhemoglobin and deoxyhemoglobin is displayed on a window 5-4. 5-5 represents a time indication bar and displaces in time axis direction in synchronism with moving picture reproduction time when the topographic image is a moving picture. The measurement amount or its variation of the measurement object substance at respective time positions can be qualitatively grasped from the scale on the ordinate axis. 5-6 represents a time indication region and displays the time indicated by the time indication bar in numerical value.

Further, after designating the time designation bar 5-5 with the mouse pointer and when displacing the bar to a desired time, the direction of time axis for reproducing a moving picture can be selected both in positive and negative directions.

With the above measure, the time dependency of the measurement amount or the measurement amount variation of the measurement object substance can be evaluated qualitatively and in detail.

Instead of the graphic display of the time dependency of the measurement amount or the measurement amount variation of the measurement object substance at one position within the measurement region, after selecting a plurality of positions with the mouse pointer the time dependency of the measurement amount or the measurement amount variation of the measurement object substance at the plurality of positions can be displayed. Through such display, a moving picture showing the measurement amount or the measurement amount variation of the measurement object substance and the time dependency of the measurement amount or the measurement amount variation of the measurement object substance at a plurality of specific position in the moving picture can be obtained at the same time, thereby, the analyzing personnel can accurately grasp many physical information data obtained from the subject.

Figure 6:
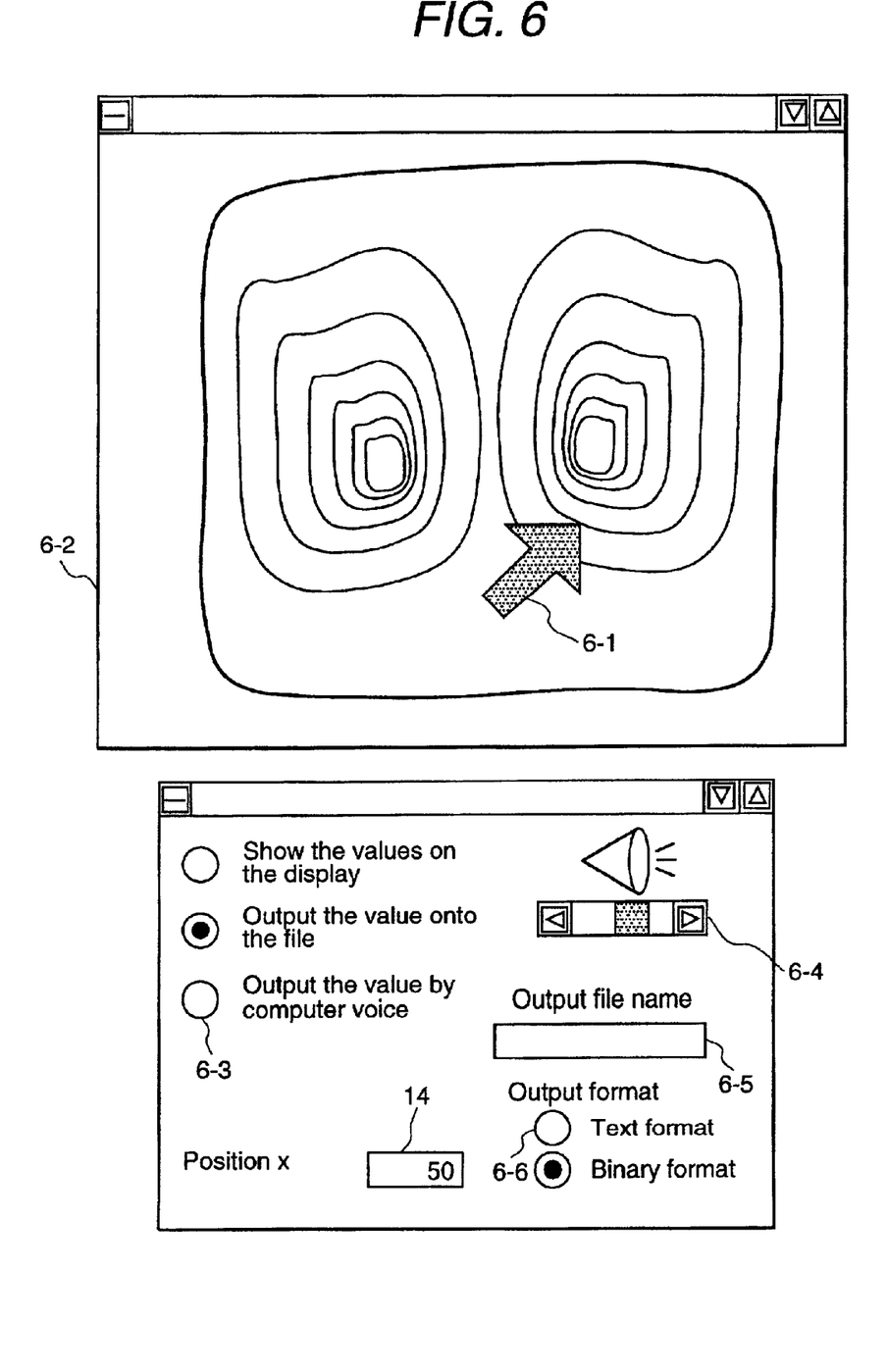
FIG. 6 is a diagram showing a still further example of a screen image displayed on a display unit in an information presentation portion in FIG. 9.

FIG. 6 shows a still further example of screen images displayed on a display unit in the information presenting portion 111 in FIG. 9. The present example enables selection of presentation types of the measurement amount or the measurement amount variation of the measurement object substance at the position selected by a pointer 6-1. Namely, through selectively pressing a presentation type selection buttons 6-3 in a window 6-2, the measurement amount or the measurement amount variation is either displayed on the screen, stored in a file or audibly informed to the operator. Of course, the measurement amount or the measurement amount variation can be designed to be outputted through a printer serving a printing means so that the same can be outputted such as to other measurement control devices and computers through a communication line represented by an internet. When the measurement amount or its variation is desired to be displayed on the screen, the same is displayed on the display region (see FIGS. 1, 2 and 4). When the measurement amount or its variation is desired to be outputted in audible type, the volume of the output voice can be adjusted through displacing the cursor of a volume adjusting portion 6-4 or pressing buttons at both ends thereof. When the measurement amount or its variation is desired to be outputted in a file format, the file name is designated at a file name designation region 6-5. Further, with regard to the output format thereof, such as text format and binary format can be selected through button operation of an output format selection portion 6-6. Further, as another output format a compressed file format can be enumerated.

Figure 7:
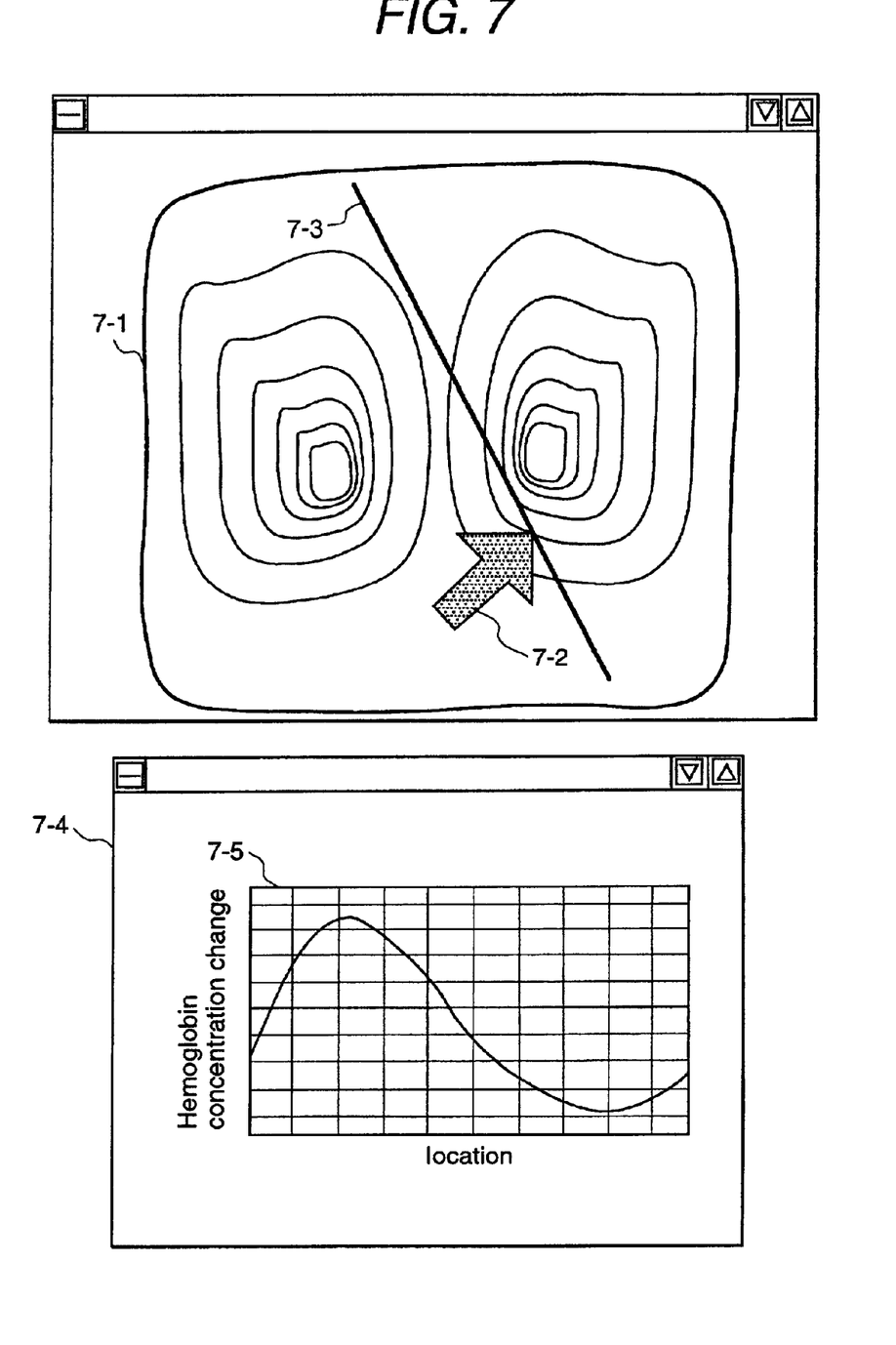
FIG. 7 is a diagram showing a still further example of a screen image displayed on a display unit in an information presentation portion in FIG. 9.

FIG. 7 shows a still further example of screen images displayed on a display unit in the information presenting portion 111 in FIG. 9. The present example displays the measurement amount or its variation of the measurement object substance on a one dimensional region within the measurement region. A one dimensional line 7-3 is drawn on a topographic image 7-1 showing measurement amount or its variation of the measurement object substance by making use of a pointing device 7-2 represented by a mouse. In the drawing, although a straight line is exemplified, a curved line can be drawn. The measurement amount or its variation of the measurement object substance at positions on the straight line is displayed in a form of graph 7-5 on another window 7-4. The ordinate represents the measurement amount or its variation of the measurement object substance (for example, hemoglobin concentration change) and the abscissa represents positional information of one dimensional shaped line 7-3. With the present measure, the measurement amount or its variation at respective positions along the one dimensional shaped line 7-3 can be grasped visually from another point of view.

Figure 8:
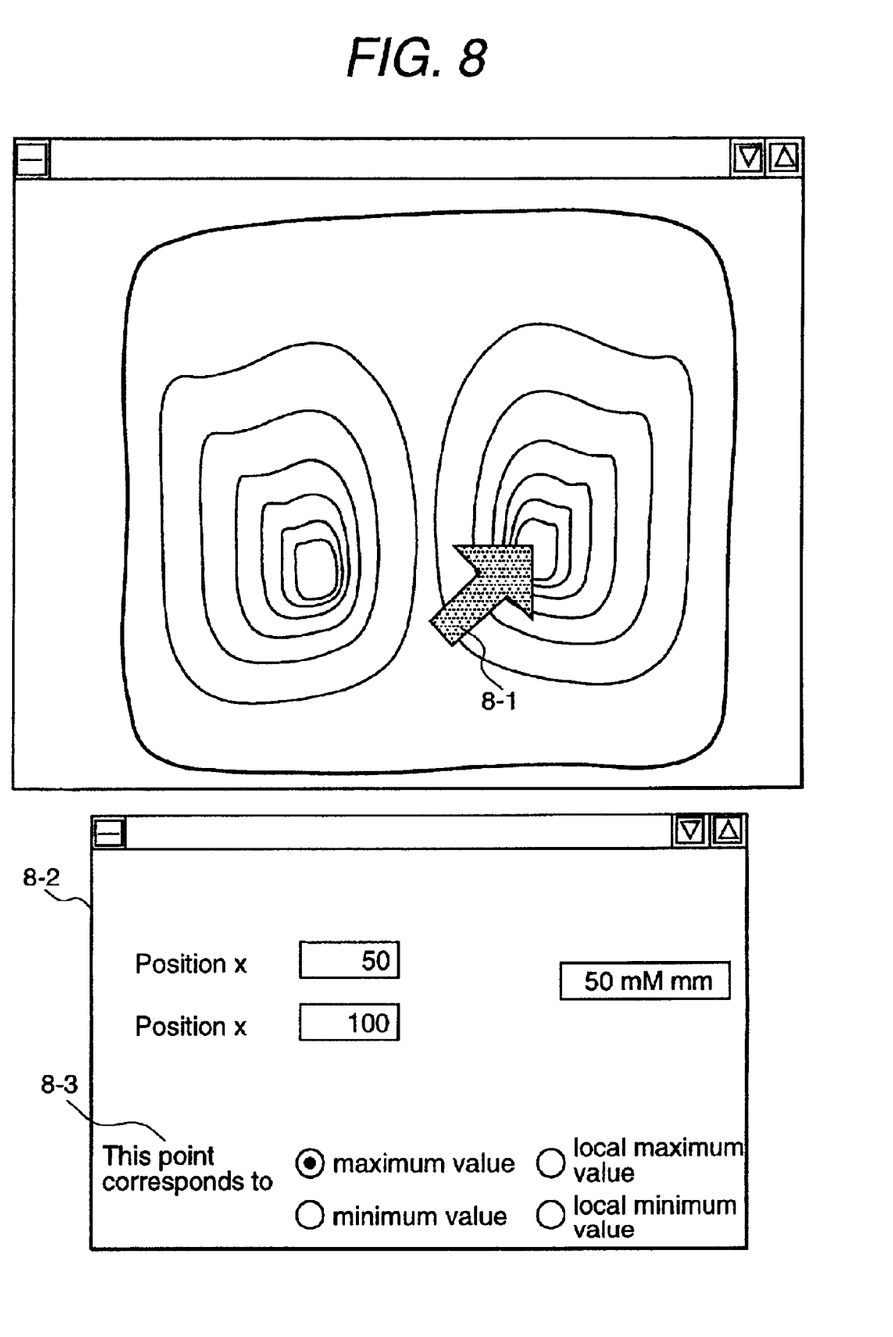
FIG. 8 is a diagram showing a still further example of a screen image displayed on a display unit in an information presentation portion in FIG. 9.

FIG. 8 is a still further example of screen images displayed on a display unit in the information presenting portion 111 in FIG. 9. The present example, when the measurement amount or its variation of the measurement object substance at a position designated and selected by a pointer 8-1 corresponds to a singular value represented by such as maximum value, minimum value and zero point, is designed to display such information on the screen of the window 8-2. Namely, when the measurement amount or its variation of the measurement object substance at the position designated and selected by the pointer 8-1 corresponds to the maximum value, the minimum value, a local maximum value, a local minimum value, zero point or a desired value designated by the analyzing personnel, a corresponding button in a display region 8-3 arranged on the screen of the window 8-2 is automatically pressed, accordingly, with the button pressed state it is recognized what sort of value is the measurement amount or its variation of the measurement object substance at the position selected by the pointer 8-1.

Instead of displaying on the screen what sort of singular value is the measurement amount or its variation of the measurement object substance at the selected position, such information can be transferred to the data analyzing personnel by means of voice other than the screen display. Further, instead of dividing the windows into two, the information on the two windows can be displayed on a single window.

In order to facilitate understanding of the present invention, symbols used will be explained briefly hereinbelow:

1-1: window including topographic image, 1-2: topographic image, 1-3: window indicating measurement value or its change, 1-4: mouse pointer, 1-5: assistant line to visually indicate coordinate information in horizontal and vertical directions of the position pointed by mouse pointer, 1-6: character series to inform sort of data desired to be displayed, 1-7: values indicating measurement value or its change, 2-1: window including topographic image, 2-2: lines in horizontal and vertical directions, 2-3: scale for measuring horizontal location and vertical location, 2-4: window for indicating measurement value or its change and/or information of location, 2-5: four buttons to control horizontal and vertical location of two lines (2-2), 2-6: pointer, 2-7: message indication area of coordinate information in horizontal (X) and vertical (Y) directions of intersection point of two lines (2-2), 2-8: coordinate information indication area of intersection point of two lines (2-2), 2-9: indication area of measurement value or its change, 3-1: optical fiber, 3-2: sensor of piezoelectric element, 3-3: subject, 3-4: pointing means, 4-1: window of which size is flexibly changed, 4-2: topographic image, 4-3: pointing means, 4-4: indication area, 5-1: windows, 5-2: topographic image, 5-3: graph showing time dependence of measurement amount variation, 5-4: window showing graph of time dependence of measurement amount variation, 5-5: time indication bar, 5-6: time display area, 6-1: pointer, 6-2: window, 6-3: presentation type selection button, 6-4: volume adjusting portion, 6-5: file name display area, 6-6: output format selection portion, 7-1: topographic image, 7-2: pointing device, 7-3: one dimensional line, 7-4: window, 7-5: graph, 8-1: pointer, 8-2: window, 8-3: indication area, 91: light source, 99: subject, 98-1~4: optical fibers for illumination, 100-1~5: optical fibers for detection, 101-1~5: photo diodes, 102: lock-in amplifier module, 106: sample hold circuit module, 107: switch, 108: A/D converter, 109: computer, 110: storage unit, 111: information presenting portion, 112: control unit.

INDUSTRIAL FEASIBILITY

According to the present invention, an optical measurement device is provided which through enabling evaluation of physical amount of a measurement object substance at any point of a subject enhances a spatial resolution and thereby permits to obtain detail information of the subject.

What is claimed is:

1. An optical measurement device which optically measures a measurement object substance within a measurement region of a subject, comprising:
    illuminating means for sending out a light to illuminate the subject;
    detecting means for detecting at least one reflected or scattered light from the illuminated subject;
    determining means for determining at least one measurement amount or measurement amount variation of the measurement object substance at a measurement position according to a detection value detected at a detection position by the detecting means;
    displaying means for displaying on a first image screen a mapping image formed by connecting points with an equal measurement amount or measurement amount variation as determined by the determining means; and
    designating means for designating at least one position on the mapping image or in the measurement region of the subject so as to visually output m a second image or audibly output a numerical value of the measurement amount or the measurement amount variation of the measurement object substance at the position designated.

2. An optical measurement device according to claim 1, wherein a plurality of measurement amounts or measurement amount variations of the measurement object substance at the position designated are taken within a time period and displayed.

3. An optical measurement device according to claim 1, wherein the light having a plurality of wavelengths and said reflected or scattered light is detected by the detected means then separated into light components of corresponding plurality of wavelengths by the determining means.

4. An optical measurement device according to claim 1, wherein the measurement amount or the measurement amount variation of the measurement object substance at the position designated is displayed in the first image screen.

5. An optical measurement device according to claim 1, wherein the measurement amount or the measurement amount variation of the measurement object substance at the position designated is displayed in a second image screen.

6. An optical measurement device according to claim 1, wherein a pair of horizontal and vertical lines passing through the designated position are displayed on the first image screen.

7. An optical measurement device according to claim 6, scales for reading horizontal and vertical positions on the horizontal and vertical lines are displayed on the first image screen.

8. An optical measurement device according to claim 1, further comprising:
- a sensor for sensing said at least one measurement position in the measurement region of the subject as designated by the designating means, said sensor being made from a piezoelectric clement and placed under a contact or non-contact condition to the subject; and
- optical fibers passing through the sensor to the subject for transmitting the light from the illuminating means onto the illumination position within the measurement region and for outputting a detection value detected by the detecting means at the detection position.

9. An optical measurement device according to claim 1, wherein the designating means designated a plurality of positions constituting a line on the mapping image so as to display in the second image measurement amounts or measurement amount variations of the measurement object substance at the positions of the line.

10. An optical measurement device according to claim 1, wherein the designating means designated a position corresponding to one of a maximum value, a minimum value, a local maximum value and a local minimum value, said one of the maximum value, the minimum value, the local maximum value and the local minimum value is displayed.

11. An optical measurement device according to claim 1, further comprising voice outputting means for outputting audibly the measurement amount or the measurement amount variation of the measurement object substance at the position designated.

12. An optical measurement device according to claim 10, further comprising voice outputting means for outputting audibly said one of the maximum value, the minimum value, the local maximum value and the local minimum value.

13. An optical measurement device according to claim 1, wherein coordinates of the position designated are displayed.

14. An optical measurement device according to claim 1, wherein the determining means selectively determines one measurement amount of the measurement object substance by linearly interpolating detection values detected at detection portions by the detecting means.

15. An optical measurement device according to claim 8, further comprising:
- a display for displaying on a first image screen a mapping image formed by connecting points with an equal measurement amount or measurement amount variation as determined by the determining means.

16. An optical measurement device according to claim 15, further comprising:
- a pointing device for designating at least one position on the mapping image so as to visually output in a second image or audibly output a numerical value of the measurement amount or the measurement amount variation of the measurement object substance at the position designated.

17. An optical measurement device according to claim 16, further comprising voice outputting means for outputting audibly the measurement amount or the measurement amount variation of the measurement object substance at the position designated.

* * * * *